United States Patent [19]

Biefeld et al.

[11] 3,949,140
[45] Apr. 6, 1976

[54] ORGANO SILICON DERIVATIVES COATED ON GLASS FIBERS

[75] Inventors: Lawrence P. Biefeld, Toledo; Kevin M. Foley, Hebron; Frank Paul McCombs, Granville, all of Ohio

[73] Assignee: Owens-Corning Fiberglas Corporation, Toledo, Ohio

[22] Filed: May 6, 1974

[21] Appl. No.: 467,311

[52] U.S. Cl. ............... 428/378; 57/140 G; 57/153; 260/3; 260/37 R; 260/42.15; 260/448.2 N; 260/448.8 R; 260/558 H; 260/561 H; 428/292; 428/295; 428/391; 428/392
[51] Int. Cl.² ..................... B32B 17/04; C07F 7/18
[58] Field of Search.. 260/448.2 N, 448.8 R, 558 H, 260/561 H, 3, 42.5, 37 R; 117/126 GS, 126 GN, 72; 428/292, 295, 378, 391, 392; 57/140 G, 153

[56] References Cited
UNITED STATES PATENTS

| | | | |
|---|---|---|---|
| 2,946,701 | 7/1960 | Plueddemann | 117/126 GS |
| 2,950,986 | 8/1960 | Bailey | 260/448.2 N |
| 2,953,570 | 9/1960 | Rudner | 260/561 H |
| 2,955,108 | 10/1960 | Omietowski | 260/583 B |
| 2,972,598 | 2/1961 | Morehouse | 260/448.2 N |
| 3,032,577 | 5/1962 | Morehouse | 260/448.2 N |
| 3,215,718 | 11/1965 | Ryan | 260/448.2 N |
| 3,259,518 | 7/1966 | Sterman | 260/448.2 N |
| 3,373,137 | 3/1968 | Soam | 260/488.2 N |
| 3,555,051 | 1/1971 | Morsden | 260/448.8 R |
| 3,555,095 | 1/1971 | Slagel | 260/584 R |
| 3,561,996 | 2/1971 | Young | 117/72 |
| 3,565,868 | 2/1971 | Sedor | 260/78.3 |
| 3,567,671 | 3/1971 | Janetos | 117/126 GB |
| 3,580,920 | 5/1971 | Culpepper | 260/448.2 N |
| 3,637,779 | 1/1972 | LeGrow | 260/448.2 N |
| 3,700,711 | 10/1972 | Berger | 260/448.8 R |
| 3,706,797 | 12/1972 | McKillip | 260/558 H |
| 3,706,800 | 12/1972 | Hartlage | 260/558 H |
| 3,715,343 | 2/1973 | Slagel | 260/88.1 PN |
| 3,734,763 | 5/1973 | Plueddemann | 117/126 GN |
| 3,756,994 | 9/1973 | Culbertson | 260/82.1 |

OTHER PUBLICATIONS

"Aminimides Show Broad Commercial Potential" in Chemical & Engineering News, Vol. 51, Apr. 2, 1973, pp. 11–12.

*Primary Examiner*—Ralph Husack
*Assistant Examiner*—William H. Schmidt
*Attorney, Agent, or Firm*—John W. Overman; Keith V. Rockey

[57] ABSTRACT

Organo silicon compounds prepared by reaction of a dialkyl hydrazine of the formula

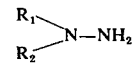

wherein $R_1$ and $R_2$ are each alkyl with an epoxy silane such as an epoxy silane of the formula

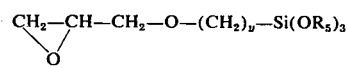

or an epoxy silane of the formula

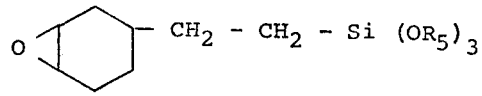

where $y$ is an integer and $R_5$ is alkyl. The organo silicon compounds described can be employed in the treatment of glass fibers to improve the bonding relationship between glass fibers and resins or elastomeric materials.

21 Claims, No Drawings

ORGANO SILICON DERIVATIVES COATED ON GLASS FIBERS

This invention relates to aminimides, and more particularly to organo silicon derivatives of aminimides.

In the April, 1973 issue of Chemical and Engineering News, there is described a method for the preparation of aminimides using dimethyl hydrazine and an epoxide. The reaction involves the formation of inner salts as follows:

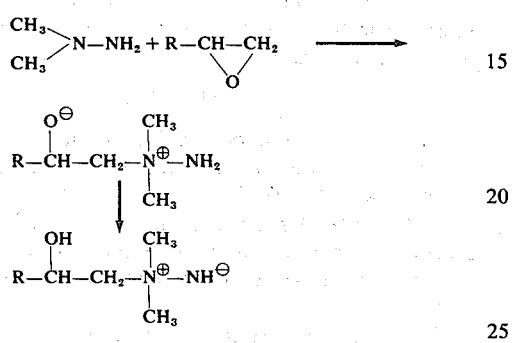

which can be reacted in situ with a carboxylic acid ester to form the corresponding aminimide in accordance with the following reaction

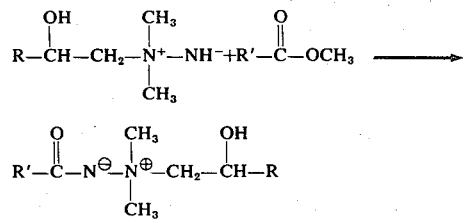

It has now been found that organo silicon compounds can be prepared by reaction of an organo silane containing an epoxy group with a dialkyl hydrazine.

It is an object of the present invention to provide a new class of organo silicon compounds, and it is a more specific object of the invention to provide a new class of organo silicon compounds by reaction of an epoxy silane with a dialkyl hydrazine.

It is another object of the invention to provide a new class of organo silicon compounds for use in assuring a more secure bond between glass fibers and resinous plastics and elastomeric materials.

The concepts of the present invention reside in a new group of organo silicon compounds prepared by reaction of an organo silane and a dialkyl hydrazine. The structures of the resulting products are not fully understood with certainty, but it is believed that the resulting product contains the grouping

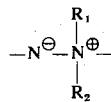

wherein $R_1$ and $R_2$ are the same as alkyl groups of the dialkyl hydrazine. The compounds are hydrolyzable in water, and consequently can be used as coupling agents in the bonding of hydrophilic materials, such as glass fibers, to hydrophobic materials, such as resinous plastics and rubbers.

As the epoxy silane, use can be made of a number of such silanes which are commercially available. Such silanes generally include at least one organic group bonded directly to the silicon atom, with at least one of the organic groups containing an epoxy group. Also attached directly to the silicon atom are 1 to 3 hydrolyzable groups, preferably lower alkoxy groups, with any remaining valences on the silicon atom being taken up by hydrogen atoms.

Such silanes may be represented by the general formula

wherein $R_3$ is an organic group containing an epoxy group, $R_4$ is alkyl (e.g., methyl, ethyl, propyl, etc.), hydrogen or lower alkoxy containing 1 to 4 carbon atoms, and Z is a lower alkoxy group containing 1 to 4 carbon atoms (e.g., methoxy, ethoxy, propoxy, etc.). Any of a variety of organic groups substituted with an epoxy group can constitute $R_3$ in the foregoing formula. For example, $R_3$ can be a glycidoxy alkyl group, an epoxy alkyl group, an epoxy cycloalkyl group, etc. In general, $R_3$ preferably contains 3 to 10 carbon atoms.

Preferred silanes are those in which $R_4$ is an alkoxy group and $R_3$ is a glycidoxyalkyl group. These silanes have the formula

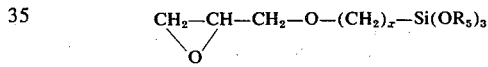

wherein $x$ is an integer from 3 to 6, and $R_5$ is $C_1$ to $C_4$ alkyl (e.g., methyl, ethyl, propyl, isopropyl, etc.).

Representative epoxy silanes include the following:
γ-glycidoxypropyltriethoxysilane
γ-glycidoxypropylethyldiethoxysilane
Δ-glycidoxybutyltrimethoxysilane
Δ-glycidoxybutyldimethoxysilane
3,4-epoxycyclohexylethyltrimethoxysilane.
gamma-glycidoxypropyltrimethoxysilane.

Also suitable are epoxy silanes having the formula

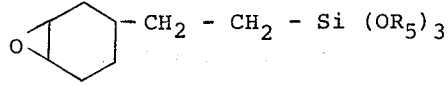

wherein $R_5$ is alkyl.

The dialkyl hydrazine employed in the practice of the invention generally has the formula

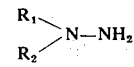

wherein $R_1$ and $R_2$ are each alkyl groups, preferably containing 1 to 8 carbon atoms, and most preferably 1 to 4 carbon atoms (e.g., methyl, ethyl, isopropyl, etc.)

The reaction can be carried out by simply contacting the epoxy silane with the desired hydrazine. The reaction can be accelerated by heating to a temperature of 30° to 120°C, depending somewhat on the boiling point of the silane; room temperatures can also be employed. Temperatures of 10° to 120°C can be employed with good results.

The reactant proportions are not critical to the practice of this invention. Generally, use is preferably made of substantially stoichiometric proportions although the reaction can be carried out using a molar ratio of the dialkyl hydrazine to epoxy silane within the range of 0.7 to 1.4, and preferably 0.9 to 1.1.

The reaction evolves an alcohol corresponding in carbon number to the alkoxy group of the silane. It is therefore believed that the product includes the structure

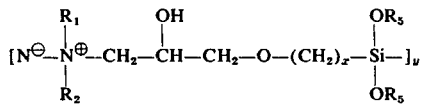

where $y$ is a value between 1 and 10. Where the reaction product is in monomeric form, it is believed the monomer has a cyclic structure

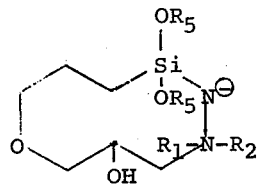

Regardless of whether the reaction product is in monomeric or polymeric form, the product can be hydrolyzed with a small amount of water to form the silanol

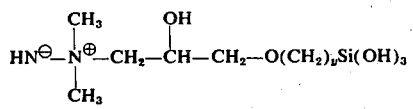

wherein the starting epoxy silane contained 3 alkoxy groups. The hydrolyzed product thus has the general formula

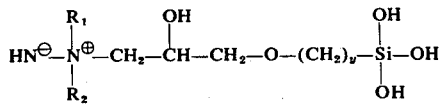

as derived from glycidoxy alkyl silanes, where $R_1$, $R_2$ and $y$ are as described above. As will be appreciated by those skilled in the art, the corresponding hydrolyzed silanol prepared when the silane is an epoxy cyclohexylsilane is more complex. The silanol produced when the epoxy silane is 3,4-epoxycyclohexylethyltrimethoxy silane has the formula

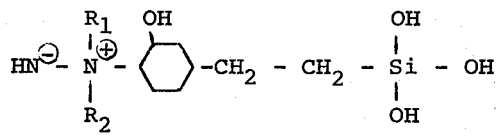

The compounds of the present invention may be used as coupling agents for bonding glass fibers to resinous plastics and elastomeric materials. It is generally preferred to apply the silane or the corresponding silanol or polysiloxane to the glass fibers, which can then be used as reinforcement for thermosetting plastics or elastomeric materials.

Having described the basic concepts of the invention, reference is now made to the following examples which are provided by way of illustration, and not of limitation, of the practice of the invention in the preparation of the organo silicon compounds of the invention and their use in the treatment of glass fibers for reinforcement of plastic and elastomeric materials.

EXAMPLE 1

Into a 1-liter, round bottom flask equipped with a stir bar, a reflux condenser, addition funnel and thermometer, there is placed 60.1 g (1.0 mole) of dimethyl hydrazine. There is then added, with stirring, 236.1 g (1.0 mole) of gamma-glycidoxypropyltrimethoxy silane. The reaction mixture is maintained for 4.25 hours at 80°C.

Thereafter, the reaction mixture is analyzed by gas chromatography, and is found to contain methanol but none of the starting materials. The product is a homogeneous solution, indicating that the product is soluble in methanol. Mass spectroscopy indicates that the predominant structure of the product is

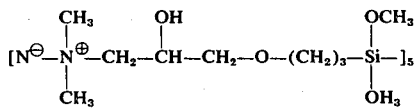

On hydrolysis with water, a silanol is produced having the formula

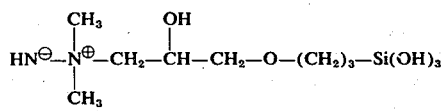

which can be further hydrolyzed to the corresponding polysiloxane.

EXAMPLE 2

Using the procedure described in Example 1, diethyl hydrazine is reacted with Δ-glycidoxybutyltriethoxy silane. The product is believed to be

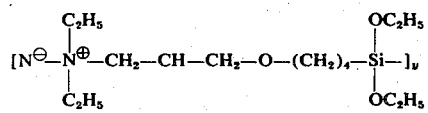

where $y$ is between 1 and 10. On hydrolysis with water, the product yields the silanol

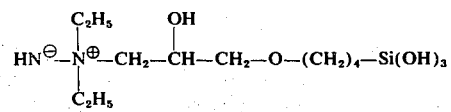

EXAMPLE 3

The procedure of Example 1 is again repreated using 3,4 epoxycyclohexylethyltrimethoxy silane and dimethyl hydrazine. The product is believed to be

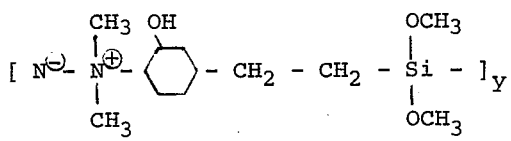

wherein y is between 1 and 10. On hydrolysis, a silanol is produced which is believed to have the formula

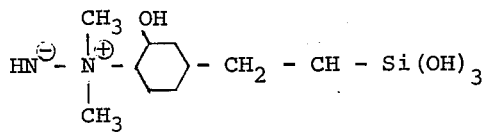

The coupling agents of the present invention are used in the same manner in which known coupling agents, such as gamma-glycidoxyisopropyltriethoxy silane, are used in the establishment of a secure bonding relationship between glass fibers and thermosetting resins or elastomeric materials. As will be appreciated by those skilled in the art, the reaction product of the present invention can be employed either in non-hydrolyzed or in hydrolyzed form.

The coupling agents of the present invention can be formulated into a variety of compositions for use in the treatment of glass fibers in the manufacture of glass fiber-reinforced resinous products including glass fiber-reinforced plastics, laminates and coated fabrics, and in the manufacture of glass fiber-reinforced elastomeric products such as drive belts, rubber tires and the like.

The term "glass fibers", as used herein, is intended to refer to and include (1) continuous fibers formed by rapid attenuation of hundreds of streams of molten glass and to strands formed when such continuous glass fiber filaments are gathered together as they are being formed; and to yarns and cords formed by plying and/or twisting a number of strands together; and to woven and non-woven fabircs which are formed of such glass fiber strands, yarns or cords, and (2) discontinuous fibers formed by high pressure steam, air or other suitable attenuating force directed onto multiple streams of molten glass issuing from a glass melting bushing or from an orifice containing spinner, and to yarns that are formed when such discontinuous fibers are gathered together to form a sliver which is drafted into a yarn; and to woven and non-woven fabrics formed of such yarns of discontinuous fibers, and (3) conbinations of such continuous and discontinuous fibers in strands, yarns, cords and fabrics formed thereof.

The coupling agents of the present invention can simply be formulated into an aqueous medium for application to the glass fibers to form a thin film. However, it is frequently preferred to formulate the silanes of the invention in combination with a film-forming material. A wide variety of film-forming materials can be used for this purpose and includes polyester resins, polyamide resins, polyolefin resins (e.g., polyethylene, polypropylene, etc.), polyepoxide resins, vinyl resins (e.g., polyvinyl chloride, polyvinyl acetate, polyvinyl alcohol, polyvinyl pyrrolidone, etc.), waxes, partially dextrinized starch as well as numerous others. Such film formers are themselves well known to those skilled in the art and are described in U.S. Pats. Nos. 2,931,739, 2,958,114, 3,040,413, 3,252,278, 3,424,608 and others. Combinations of two or more of the above film-forming materials can also be used.

The size compositions can also be formulated to include any of a variety of wetting agents, glass fiber lubricants, etc., which are likewise known to the art. The size compositions can be formulated in aqueous media or in inert organic solvents, depending on the intended use of the treated glass fibers and the nature of the film-forming binder or binders employed.

Examples of such size compositions which can be employed in the treatment of glass fibers for use in the manufacture of glass fiber reinforced resins and elastomeric products include the following:

EXAMPLE 4

Size Composition

| | Parts by weight |
|---|---|
| Product of Example 1 | 1.0 |
| Polypropylene emulsion | 5.5 |
| Water | 93.5 |

EXAMPLE 5

Size Composition

| | Parts by weight |
|---|---|
| Product of Example 3 | 1.1 |
| Wetting agent (Nopcogen 16L) | 0.1 |
| Water | 98.8 |

EXAMPLE 6

Size Composition

| | Parts by weight |
|---|---|
| Product of Example 3 (non-hydrolyzed) | 1.5 |
| Epoxy resin (DER 330) | 7.0 |
| Diacetone alcohol | 91.5 |

EXAMPLE 7

Size Composition

| | Parts by weight |
|---|---|
| Product of Example 1 | 1.5 |
| Saturated polyester resin | 3.0 |
| Polyvinyl alcohol | 1.0 |
| Wetting agent | 0.5 |
| Water | 94.0 |

EXAMPLE 8

Size Composition

| | Parts by weight |
|---|---|
| Partially dextrinized starch | 8.0 |
| Hydrogenated vegetable oil | 1.5 |
| Wetting agent | 0.5 |
| Product of Example 3 | 1.8 |
| Water | 88.2 |

In formulating size compositions with the coupling agents of the present invention, the coupling agent is generally employed in an amount constituting from 0.1 to 10% by weight of the composition, and the film-forming binder in an amount from 1% to 25% by weight of the composition. These amounts are not critical to the practice of the invention and can be varied as desired. The compositions of Examples 4 and 8 can be applied to glass fibers as they are formed or afterwards, in accordance with conventional procedures.

Glass fibers coated with the coupling agents of the present invention can be incorporated in the form of fibers, yarns, rovings, fabrics and the like with resin materials, including epoxy resins, polyester resin, polyamide resins as well as numerous other thermoplastic and/or thermosetting plastics in amounts such that the treated glass fibers constitute from 1% to 20% by weight of the plastic laminate or coated fabric formed. The coating on the individual glass fibers, comprising as the essential component the silanes of the present invention, serves to provide a secure bonding relationship between the glass fiber surfaces and the resin.

Glass fibers sized with a composition embodying the coupling agents of the present invention can also be used in the manufacture of glass fiber reinforced elastomeric products. In the preferred practice of this concept of the invention, the glass fibers which have been sized with one of the compositions of Examples 4 to 8 are formed into strands, yarns, cords formed of strands which are plied and twisted together, or threads, hereinafter referred to as bundles, are subjected to impregnation with an aqueous composition formulated to include a resorcinolaldehyde resin component and an elastomer component.

A wide variety of such impregnating compositions are well known to those skilled in the art and are described in U.S Pats. Nos. 3,402,064, 3,424,608, 3,567,671, 3,591,357 and numerous others. This concept may be illustrated by way of the folowing examples.

EXAMPLE 9

Using the procedure described in U.S. Pat. No. 3,567,671, an impregnating composition is formulated as follows:

Impregnating Composition

|  | Parts by weight (solids basis) |
|---|---|
| Resorcinol-formaldehyde resin (Penacolyte R 2170) | 5.0 |
| Vinyl pyridine-butadiene-styrene terpolymer (Gentac FS) | 30.0 |
| Vinyl chloride-vinylidene chloride copolymer (Dow Latex 874) | 20.0 |
| Microcrystalline paraffin wax | 6.0 |

Water constitutes the balance of the composition and is present in an amount sufficient to adjust the solids content of the composition to within the range of 20% to 55% solids by weight. The impregnation can be carried out in accordance with the procedure described in U.S. Pat. No. 3,424,608 whereby the solids of the impregnating composition serve to coat the fibers which have been previously sized with one of the compositions of Examples 4 to 8 and serve to separate the sized fibers each from the other to cushion athe fibers and protect the sized fibers from destruction by mutual abrasion.

EXAMPLE 10

Glass fibers sized with the composition of Example 5 are impregnated with the following impregnating composition of the type illustrated in Example 9, except that the vinyl chloridevinylidene chloride copolymer component is replaced by a dicarboxylated butadiene-styrene copolymer:

Impregnating Composition

|  | Parts by weight (solids) |
|---|---|
| Resorcinol-formaldehyde resin | 5.0 |
| Vinyl pyridine-butadiene-styrene terpolymer | 30.0 |
| Dicarboxylated butadiene-styrene copolymer (Pliolite 4121 - Goodyear) | 20.0 |
| Microcrystalline paraffin wax | 6.0 |
| Water to solids content of 35% | |

Application of this impregnating composition can be made in the amount sufficient to deposit in the glass fiber bundle solids constituting from 15 to 40% by weight of the glass fiber system.

As used herein, the term "elastomer" is intended to mean and include natural rubber in the cured and uncured stage, vulcanized or unvulcanized stage, and synthetic organic elastomeric materials such as nitriles, acrylics and esters and terpolymers thereof with styrene and acrylonitriles, styrene and vinyl pyridine; and EPDM rubbers as represented by butadiene polymers and copolymers with monoolefins such as butadiene-styrene vinyl pyridine terpolymers, chloroprene, isoprene, neoprene, isobutyl rubber and the like elastomeric polymers and copolymers in their cured or uncured stages, and vulcanized or unvulcanized stages. Included also are the EPDM rubbers, such as formed by the interpolymerization of ethylene, an alpha-monoolefin having from 3 to 20 carbon atoms, such as propylene, and polyene, such as dicyclopentadiene, 1,4-hexadiene and preferably an alkylene or alkylidene norbornene, such as 5-alkylidene-2-norbornene and the like in which the alkylidene group numbers from 2 to 12 carbon atoms, and polysulfone rubbers.

In facilitating the combination of glass fibers treated in accordance with the present invention with elastomeric materials, the individual glass fibers contaning a coating on the surfaces thereof from Examples 4 to 8 are mixed with an elastomeric material or otherwise laid down in the desired arrangement for combination with the elastomeric material, as in the manufacture of glass fiber-reinforced belts or in the manufacture of rubber tires reinforced with cords of glass fibers. The combination of glass fibers and elastomeric material is processed in a conventional manner by mold or cure under heat and compression or vulcanized for advancement of the elastomeric material to a cured or vulcanized stage while in combination with the treated glass fibers or bundles of glass fibers whereby the glass fibers or bundles of glass fibers become strongly integrated with the elastomeric materials in the glass fiber-elastomeric product.

In the final system, the elastomeric material with which the glass fibers or bundles of glass fibers are combined, constitutes a continuous phase. Such continuous phase elastomeric materials may comprise elastomers or rubbers of the type incorporated into treating compositions or the elastomeric material can differ therefrom. It is believed that the tie-in between the individually coated glass fibers or the impregnated bundles of glass fibers and the elastomeric materials forming the continuous phase occurs primarily during cure or vulcanization of the elastomeric material in combination with the treated glass fibers.

It will be apparent that various changes and modifications can be made in the details of procedure, formulation and use without departing from the spirit of the invention, especially as defined in the following claims.

What is claimed is:

1. Glass fibers having a thin size coating thereon, said coating formed from a silicon compound prepared by reaction of (1) a dialkyl hydrazine having the formula

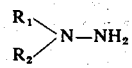

wherein $R_1$ and $R_2$ are each alkyl groups containing 1 to 8 carbon atoms with (2) an epoxy silane having the formula

wherein $R_3$ is an organic group containing an epoxy group and containing 3 to 10 carbon atoms, $R_4$ is selected from the group consisting of alkyl, hydrogen and lower alkoxy and Z is a lower alkoxy group, with the molar ratio of the dialkyl hydrazine to the epoxy silane being within the range of 0.7 to 1.4.

2. Glass fibers as defined in claim 1 wherein the coating also contains a film-forming material.

3. Glass fibers as defined in claim 1 wherein the coating also contains a glass fiber lubricant.

4. Glass fibers as defined in claim 1 wherein the epoxy silane is a silane of the formula

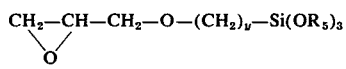

wherein $y$ is an integer from 3 to 6 and $R_5$ is $C_1$–$C_4$ alkyl.

5. Glass fibers as defined in claim 1 wherein the epoxy silane is a silane having the formula

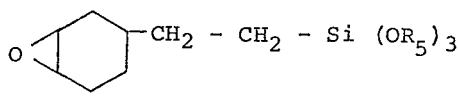

where $R_5$ is lower alkyl.

6. Glass fibers as defined in claim 1 wherein the epoxy silane is gamma-glycidoxypropyltrimethoxy silane.

7. A glass fiber bundle comprising a plurality of glass fibers, each of the individual fibers having a thin size coating on the surfaces thereof, said coating comprising an organo silicon compound prepared by reaction of (1) a dialkyl hydrazine having the formula

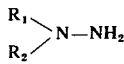

wherein $R_1$ and $R_2$ are each alkyl groups containing 1 to 8 carbon atoms with (2) an epoxy silane having the formula

wherein $R_3$ is an organic group containing an epoxy group and containing 3 to 10 carbon atoms, $R_4$ is selected from the group consisting of alkyl, hydrogen and lower alkoxy and Z is a lower alkoxy group, with the molar ratio of the dialkyl hydrazine to the epoxy silane being within the range of 0.7 to 1.4, and an impregnant in the bundle, said impregnant comprising a blend of an elastomer and a resorcinol-aldehyde resin.

8. A bundle as defined in claim 7 wherein the bundle is formed of a plurality of strands of glass fibers.

9. A bundle as defined in claim 8 wherein the strands have been twisted and plied together.

10. A glass fiber bundle as defined in claim 7 wherein the impregnant comprises a blend of a resorcinol-formaldehyde resin, a vinyl pyridine-butadiene-styrene terpolymer, a microcrystalline wax and a polymeric material selected from the group consisting of a vinyl chloride-vinylidene chloride copolymer and a carboxylated butadiene-styrene copolymer.

11. A glass fiber bundle as defined in claim 10 wherein the polymeric material is a carboxylated butadienestyrene copolymer.

12. A glass fiber bundle as defined in claim 7 wherein the epoxy silane is a silane of the formula

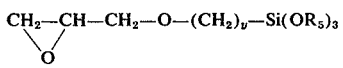

wherein $y$ is an integer from 3 to 6 and $R_5$ is $C_1$–$C_4$ alkyl.

13. A glass fiber bundle as defined in claim 7 wherein the epoxy silane is a silane having the formula

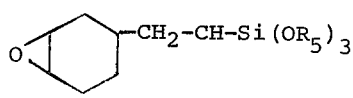

where $R_5$ is lower alkyl.

14. In a glass fiber reinforced product in which an elastomer or a thermosetting or thermoplastic resin constitutes a continuous phase in which the glass fibers are distributed, the improvement in the bonding relationship between the glass fibers and the elastomer or resin comprising a coating on the glass fibers comprising an organo silicon compound prepared by reaction of (1) a dialkyl hydrazine having the formula

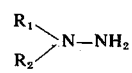

wherein $R_1$ and $R_2$ are each alkyl groups containing 1 to 8 carbon atoms with (2) an epoxy silane having the formula

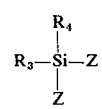

wherein $R_3$ is an organic group containing an epoxy group and containing 3 to 10 carbon atoms, $R_4$ is selected from the group consisting of alkyl, hydrogen and lower alkoxy and Z is a lower alkoxy group, with the molar ratio of the dialkyl hydrazine to the epoxy silane being within the range of 0.7 to 1.4.

15. In a glass fiber reinforced product as defined in claim 20 wherein the epoxy silane is a silane of the formula

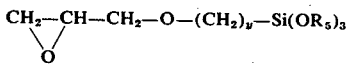

wherein y is an integer from 3 to 6 and $R_5$ is $C_1$–$C_4$ alkyl.

16. In a glass fiber reinforced product as defined in claim 20 wherein the epoxy silane is a silane having the formula

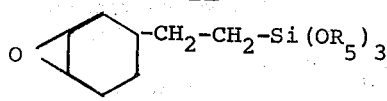

wherein $R_5$ is lower alkyl.

17. A product as defined in claim 14 wherein the product is a glass fiber reinforced elastomer.

18. A product as defined in claim 17 wherein the glass fibers are in the form of bundles, with said coating being present on the individual fibers.

19. A product as defined in claim 18 wherein the bundles include as elastomer compatible impregnant therein.

20. A product as defined in claim 18 wherein the bundles are formed of a plurality of strands of glass fibers.

21. A product as defined in claim 20 wherein the strands have been twisted and plied together.

* * * * *